(12) United States Patent
Farmer et al.

(10) Patent No.: US 7,186,989 B2
(45) Date of Patent: Mar. 6, 2007

(54) LOW THERMAL MASS FLUOROMETER

(75) Inventors: Andrew Farmer, St. Petersburg, FL (US); David P. Fries, St. Petersburg, FL (US); Bill Flanery, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/908,994

(22) Filed: Jun. 3, 2005

(65) Prior Publication Data

US 2005/0269522 A1 Dec. 8, 2005

Related U.S. Application Data

(60) Provisional application No. 60/521,602, filed on Jun. 3, 2004.

(51) Int. Cl.
*G01J 1/58* (2006.01)
(52) U.S. Cl. .................... 250/458.1; 356/417
(58) Field of Classification Search ............... 356/417; 250/458.1
See application file for complete search history.

(56) References Cited

U.S. PATENT DOCUMENTS

| | | | | |
|---|---|---|---|---|
| 4,895,156 A | * | 1/1990 | Schulze | 250/458.1 |
| 5,639,428 A | * | 6/1997 | Cottingham | 422/112 |
| 5,686,724 A | * | 11/1997 | Spilker et al. | 250/255 |
| 6,403,037 B1 | * | 6/2002 | Chang et al. | 422/68.1 |
| 2004/0222384 A1 | * | 11/2004 | Lee et al. | 250/458.1 |

FOREIGN PATENT DOCUMENTS

JP 2001042498 A * 2/2001

OTHER PUBLICATIONS

Belgrader et al., "A Battery-Powered Notebook Thermal Cycler for Rpaid Multiplex Real-Time PCR Analysis", Jan. 15, 2001, Analytical Chemistry, vol. 73, pp. 286-289.*
Belgrader et al., "PCR detection of bacteria in seven minutes", Apr. 16, 1999, Science, vol. 284, Issue 5413, pp. 39-61.*
Burns et al., "An integrated nanoliter DNA analysis device", Oct. 16, 1998, Science, vol. 282, Issue 5388, pp. 54-58.*

* cited by examiner

*Primary Examiner*—Renee Luebke
*Assistant Examiner*—Mary Zetti
(74) *Attorney, Agent, or Firm*—Molly L. Sauter; Smith & Hopen, P.A.

(57) ABSTRACT

The present invention provides core technologies necessary for a portable, low cost, thermal-regulating LED-based handheld fluorometer. The regulated fluorometer is based on a low thermal mass infrared heater, and an orthogonal geometry LED based filter fluorometer. Power is supplied through an external power supply and data is collected in real-time through standard serial interfaces of personal computers or personal digital assistants. Thermal regulation is automatically maintained using temperature sensor feedback control. Optical excitation relies on LED light source(s) and optical detection is through an adjustable integrating photodetector. Such a handheld system can allow applications requiring temperature sensitive photometric measurements for real time analyte detection to be performed in the field.

17 Claims, 1 Drawing Sheet

LOW THERMAL MASS FLUOROMETER

CROSS REFERENCE TO RELATED APPLICATION

This application claims benefit of pending provisional U.S. Ser. No. 60/521,602, filed Jun. 3, 2004.

STATEMENT OF GOVERNMENT INTEREST

This invention was made with Government support under Grant No. DASG60-00-C-0089 awarded by the U.S. Army Space and Missile Defense Command. The Government has certain rights in the invention.

STATEMENT OF GOVERNMENT INTEREST

This work has been supported by USA Space Missile Defense Command (SMDC) grant DASG-60-00-C-0089.

BACKGROUND OF INVENTION

The advent of molecular biological techniques has led to a dramatic increase in the speed, efficiency and species resolution obtained in microbiological studies from virtually every environment on earth. While this has revolutionized the way microbiology is performed, a requirement for access to laboratory facilities and infrastructure still exists, thereby introducing a spatial and temporal separation between sample collection and analysis.

There has been an increasing need in the scientific and military communities to collect and analyze data in the field. In situ analysis holds many advantages over collecting samples, transporting them, and analyzing the samples in a laboratory. Timely analysis reduces degradation of the samples, permits more rapid feedback to the observer, and may reduce overall cost as well as improve the results of the analysis.

Toward achieving a truly portable sensor, several requirements must be kept in mind. The system must be operated on an internal battery or portable power; therefore the entire system must be conservative with its power usage in order to be operable for an extended period of time. There should be a method for giving feedback to the user, in order to verify the analysis is being performed properly. Preferably, a familiar graphical user interface (GUI) should be provided to display the data or other relevant information in real-time, this will allow the user to immediately interpret and react to the test results. In addition to displaying information, the data should be stored for later retrieval and further analysis on a desktop computer. To achieve widespread use, the system cost should be kept as low as possible. This is especially relevant for MEMS sensors, which take advantage of wafer-level processing capabilities, to reduce the cost of system components. To be truly portable and easily operated by the end user, the complete sensor assembly should be handheld.

As is known in the art, a filter fluorometer measures the ability of a sample to absorb light at one wavelength and emit light at a longer wavelength. A filter fluorometer is a good choice when sensitive quantitative measurements are desired for specific compounds. The comparative ease of handling and low cost make filter fluorometers ideal for dedicated and routine measurements. A fluorometer provides a relative measurement and can be calibrated with a known concentration standard or correlated to standard laboratory methods to produce quantitative measurements. Fluorometers are utilized in molecular biology for the detection and measurement of a variety of elements. In a particular application, it is known to use a filter fluorometer as a nucleic acid amplification device.

Due to the temperature sensitivity of fluorescence measurements, many fluorometers include heating and cooling capabilities. Heating systems know if the art for use in fluorometers, consist of ceramic block or resistive heaters and cooling fans. These components exhibit a high thermal mass.

Common bench top instrumentation platforms, including filter fluorometers, are large and expensive, and primarily target high throughput screening laboratory analysis. Such systems offer little recourse for laboratories operating on limited budget, tight space restrictions, small sample throughput, or to technicians collecting samples in the field. Environmental and clinical applications that require nucleic acid amplification, enzymatic studies and analytical biochemical reactions, that require precise thermal control, would benefit from a portable instrumentation system designed for these applications.

Accordingly, what is needed in the art is a portable, low cost, low thermal mass regulating fluorometer.

SUMMARY OF INVENTION

In accordance with the present invention is provided, a low thermal mass fluorometer including a reaction chamber, an infrared radiant heater positioned to supply radiant heat to the reaction chamber, an infrared thermometer positioned to monitor the radiant heat supplied to the reaction chamber by the infrared radiant heater, a temperature feedback controller coupled to the infrared radiant heater and the infrared thermometer, the temperature feedback controller coupled to the infrared radiant heater to adjust the supply of radiant heat as monitored by the infrared thermometer, a light emitting diode positioned to supply fluorescence excitation to the reaction chamber and an integrating photodetector positioned to detect fluorescence emission from the reaction chamber, the photodetector positioned geometrically orthogonal to the light emitting diode.

The present invention provides core technologies necessary for a portable, low cost, thermal-regulating LED-based handheld fluorometer. The regulated fluorometer is based on a low thermal mass infrared heater, and an orthogonal geometry LED based filter fluorometer. Power is supplied through an external power supply and data is collected in real-time through standard serial interfaces of personal computers or personal digital assistants. Thermal regulation is automatically maintained using temperature sensor feedback control. Optical excitation relies on LED light source(s) and optical detection is through an adjustable integrating photodetector. Such a handheld system can allow applications requiring temperature sensitive photometric measurements for real time analyte detection to be performed in the field.

The fluorometer core technology as disclosed is expandable to a multi spectral fluorometer system for applications needing positive or negative controls and internal calibrants. Additional bandpass filters are interchangeable to accommodate added spectral bandwidth. Detector sensitivity is achieved by the use of a tunable integrating photodetector. Thermal control is improved by incorporating a pulse-width-modulated infrared heater and a thermopile based digital thermometer for accurate temperature regulation. This non-contact design allows the sample's fluorescence to be measured without interference from the thermal control system, and improves heat distribution within the sample. Additionally, the low thermal mass of the IR-controlled heating system allows for rapid and more efficient temperature cycling, compared to the higher thermal mass systems using metallic or ceramic heat-block systems.

In accordance with the present invention is a portable device, based on a 90° filter-based fluorometer and infrared thermal cycler. The device is an improvement in that it has a low thermal mass design, which allows for passive cooling and eliminates the need for a cooling fan. The system also yields a faster response time for isothermal heating, which is important for both reaction control, minimizing unwanted side reactions and for efficient power usage. The instrument employs a simplified mini radiant heater without the use of mirrors or lenses and has been designed to accept standard reaction tubes and eliminates the need for custom fluid vials and optical cells.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figure 1:
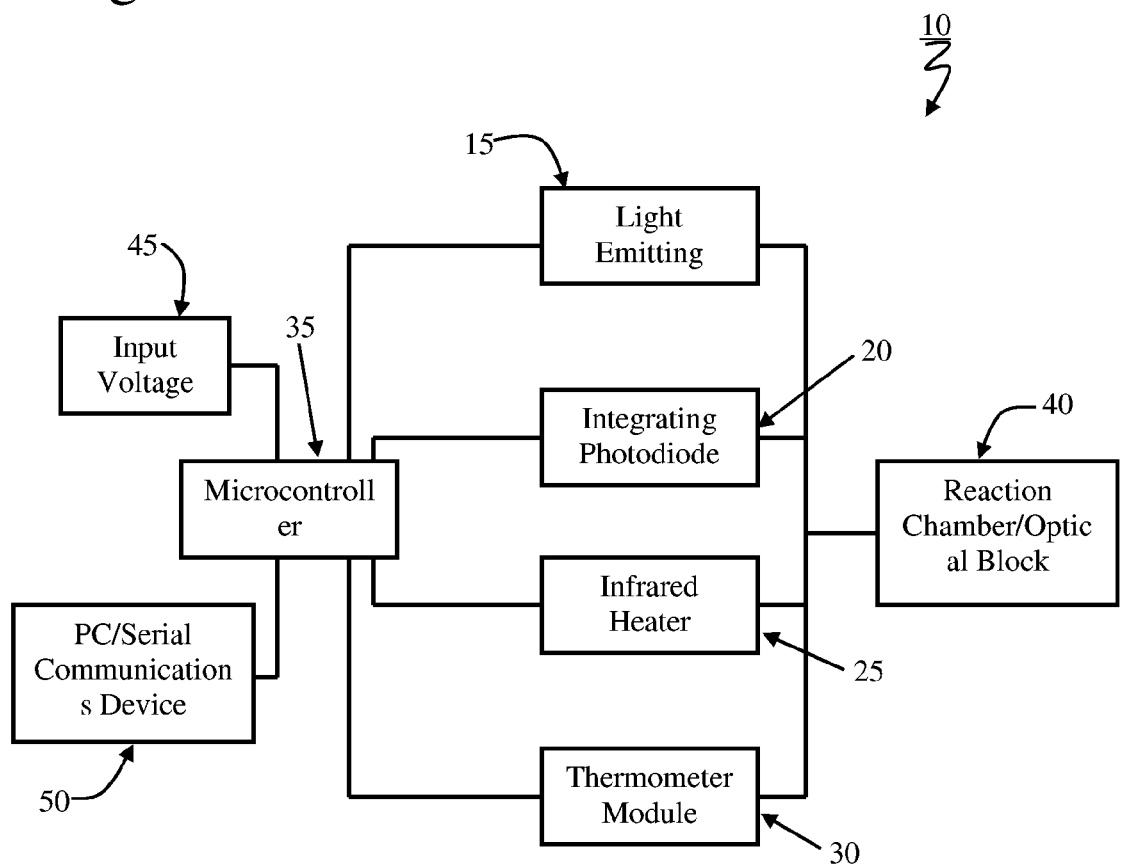
FIG. 1 is a block diagram illustrating the elements of the low thermal mass fluorometer in accordance with the present invention.

With reference to FIG. 1, in a particular embodiment the low thermal mass fluorometer 10 in accordance with the present invention incorporates a simple light emitting diode (LED) light source 15, and an integrating photodetector 20 for fluorometry. A MEMS-based infrared radiant heater 25 and an infrared thermometer module 30 make up the thermal regulation system. All of these components are controlled with custom software communicated through a microcontroller 35. In typical operation, the sample to be evaluated is placed in the reaction chamber 40. Power is supplied 45 either externally or through an integrated power supply and a serial communication interface 50 is used to provide a display for data output and a means to control the temperature cycling and optical parameters.

Figure 2:
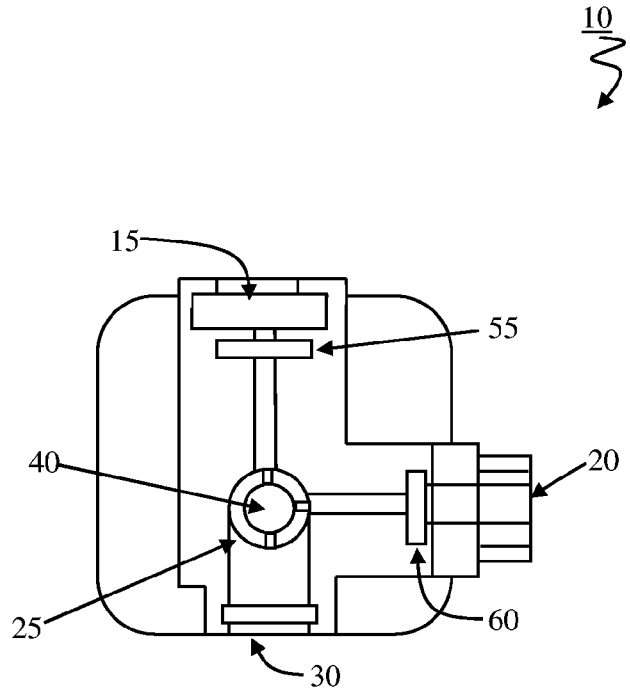
FIG. 2 is a diagrammatic view of the low thermal mass fluorometer in accordance with the present invention.

FIG. 2 illustrates the relative positioning of the elements of the low thermal mass fluorometer in accordance with the present invention. As shown the light emitting diode 15 and the photodetector 20 are positioned to be geometrically orthogonal. The light-weight, design of the interior of the block, utilizing an infrared heater 25 and a thermometer 30, allows for rapid, yet passive, transfer of heat to and from the sample volumes within the reaction chamber 40. The relative position of these components to each other negates the need for expensive lenses and mirrors. In a particular embodiment, a filter 55 is positioned to filter the infrared light emitted from the LED 15 and another filter 60 is positioned to filter the light entering the photodetector 20.

In a specific embodiment, the LED used for fluorescence excitation in the fluorometer is a high-brightness, 5 mm Ti, blue LED. The input voltage for the LED can vary, but 2.5 volts is considered typical for these devices. Fluorescence emission is detected using a blue-enhanced integrating photodiode. At 5 volts power, the photodiode has a response time of 45 ns with dark currents of 6.5 nA typ. and 26 nA max. The active detection area is 0.200 in diameter. Both the LED and the photodiode are optically isolated at 90° with 9×9 mm bandpass filters 485 nm and 530 nm respectively. These wavelengths accommodate the commonly used FAM fluorophores. The 485 nm excitation filter has a bandwidth of 22 nm and the 530 nm emission filter has a bandwidth of 30 nm. The specific elements described in accordance with this embodiment, are exemplary and are not meant to limit the scope of the claims. Various other LEDs, photodiodes and filters known in the art are within the scope of the present invention.

In accordance with a particular embodiment of the thermal system of the present invention, heat is supplied by an infrared heater with a Germanium Filter. The Germanium filter only transmits the heater-emitted light within a bandwidth of 7–12 urn to pass into the reaction chamber so as not to interfere with the fluorescence optics. The heater itself is rated for temperatures up to 850° C., but the maximum recommended operating temperature for this system is 95° C. Maximum power consumption of the heating element at 850° C. is 2.0 watts, with a maximum current of 0.77 amps. Output of heat is controlled by pulse-width modulation at a maximum of 2.6 volts. The pulse-width modulation of the heater is determined by the software, which is based on input from the user. In exemplary embodiment, each pulse begins with a 2.5 volt warming pulse, which then decays to 2.5 volts. The frequency is maintained with an on/off switch. To monitor the temperature of the reaction/optical block, a digital SPI outputting infrared thermometer module is used. An exemplary detector may exhibit a response time of 500 ms and a temperature range of 20° C. to 120° C. when operated at 5 volts. The microcontroller cycles the heater and the thermometer module so that the infrared light emitted from the heater does not contaminate the infrared being emitted from the reaction tube and chamber.

In accordance with the present invention, the software for this system is designed to give the user flexibility and control of the fluorometry and heating subsystems will accommodate a variety of thermally regulated and optical experiments. The user is given the ability to select the thermal regulations parameters. Predetermined cycles may also be selected, including a "denaturing" cycle and an "amplification" cycle. From this menu, the user can select the duration temperature the cycles are to be regulated. These inputs can be set to zero if heat is not to be used. The user can also test the performance and calibrate the heater system utilizing the customized software.

In addition to the thermal parameters, the user also has the option to select the optical parameters through the software. The user can enter the desired integration time of the photodiode signal. These signals can then be averaged as defined by the user. Averaging can be used to lower the noise in the data text read outputted. Here the user also sets the number of times the system is to gather this averaged data as well as the time between each read.

In typical operation of the low thermal mass fluorometer in accordance with the present invention, field samples are processed by the user external to the photometer and are introduced into the heated fluorimetric detector region using industry standard optical grade polypropylene PCR tubes. The control software for the handheld can be modified to accommodate a variety of thermal cycling and temperature regulation requirements. Data output is in raw counts and is calibrated by the user. The device is capable of providing in-the-field analytics for qualitative and quantitative measurements. For quantitative fluorescent probe, natural fluorescence and tracer studies, the instrument can be used to generate sample and calibration graphs. Quantification of common nucleic acid amplification data (PCRJNASBA) for nucleic acid concentrations and therefore cell concentration is also possible. Quantification of threshold cycle detection times can be achieved through the use of standard curves and clustering analysis to achieve orders of magnitude resolution.

In a specific application of the invention, the low thermal mass fluorometer is used as an NASBA sensor. Nucleic acid sequence based amplification (NASBA) is an isothermal amplification strategy that has the ability to selectively amplify target RNA in the presence of contaminating DNA. Using the thermally regulated fluorometer in accordance with the present invention, along with a personal digital assistant, a sensor unit is provided for detecting real-time NASBA. The NASBA sensor contains two important sections: Thermal regulation—which regulates the temperature of the sample so amplification can occur; and fluorescence excitation and detection—which optically excites the sample and reads the resulting fluorescence signal. With reference again to FIG. 2, the photodiode detector 20, LED 15 and associated band pass filters 55, 60 allow detection of fluorescence, while the infrared heater 25 and thermometer 30 regulate the temperature. The sample is inserted in a slot centered directly above the IR heater 25 and centered in the LED 15 light path and detector field of view.

The need for rapid detection of target analytes in the field has yielded a thermal regulating fluorometer for photometric analysis as shown and described by the present invention. The low mass of the opto-thermal system provides the basis for rapid sample heating with rapid, yet passive cooling. The design and layout can be expanded to incorporate multiple sample tubes as well as multiple fluorescent signal sets. The thermal control, combined with the fluorescence detection system, provides the basis for an inexpensive, portable device that is suitable for on-site analysis.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A low thermal mass fluorometer, the fluorometer comprising:
   a reaction chamber;
   an infrared radiant heater positioned to supply radiant heat to the reaction chamber;
   an infrared thermometer positioned to monitor the radiant heat supplied to the reaction chamber by the infrared radiant heater;
   a temperature feedback controller coupled to the infrared radiant heater and the infrared thermometer, the temperature feedback controller coupled to the infrared radiant heater to adjust the supply of radiant heat as monitored by the infrared thermometer;
   a light emitting diode positioned to supply fluorescence excitation to the reaction chamber; and
   an integrating photodetector positioned to detect fluorescence emission from the reaction chamber, the photodetector positioned geometrically orthogonal to the light emitting diode.

2. The fluorometer of claim 1, wherein the reaction chamber is dimensioned to accommodate a standard polymerase chain reaction tube.

3. The fluorometer of claim 1, wherein the infrared radiant heater further comprises a bandpass filter to pass infrared heat into the reaction chamber within a bandwidth that does not interfere with the light supplied by the light emitting diode.

4. The fluorometer of claim 1, wherein the infrared radiant heater is a pulse-width modulated infrared radiant heater.

5. The fluorometer of claim 1, wherein the infrared radiant heater is a MEMS-based infrared heater.

6. The fluorometer of claim 1, wherein the infrared thermometer is a thermopile based digital thermometer.

7. The fluorometer of claim 1, wherein the light emitting diode is a 5 mm Ti, blue light emitting diode.

8. The fluorometer of claim 1, further comprising a bandpass filter positioned to optically isolate the light emitted from the light emitting diode.

9. The fluorometer of claim 8, wherein the bandpass filter is a 485 nm bandpass filter.

10. The fluorometer of claim 1, wherein the integrating photodetector is a blue-enhanced integrating photodiode.

11. The fluorometer of claim 1, further comprising a bandpass filter positioned to optically isolate the fluorescence emission received by the integrating photodiode.

12. The fluorometer of claim 11, wherein the bandpass filter is a 505 nm bandpass filter.

13. The fluorometer of claim 1, further comprising a control software module in circuit communication with the temperature feedback controller, the light emitting diode and the integrating photodetector.

14. The fluorometer of claim 1, further comprising an external power supply.

15. The fluorometer of claim 1, further comprising an integrated power supply.

16. The fluorometer of claim 1, further comprising a serial communication module in circuit communication with the integrating photodetector.

17. The fluorometer of claim 12, further comprising an output display in communication with the serial communication module, the output display to present the fluorescence emitted from the reaction chamber.

* * * * *